United States Patent [19]

Smith et al.

[11] Patent Number: 5,157,163

[45] Date of Patent: Oct. 20, 1992

[54] PURIFICATION OF METHYL TERTIARY-BUTYL ETHER

[75] Inventors: William A. Smith; Roya Tooloian, both of Houston, Tex.

[73] Assignee: Texaco Chemical Company, White Plains, N.Y.

[21] Appl. No.: 770,217

[22] Filed: Oct. 3, 1991

[51] Int. Cl.⁵ .............................................. C07C 41/34
[52] U.S. Cl. ..................... 568/699; 568/698; 203/92; 203/96
[58] Field of Search ................. 568/699, 698; 203/92, 203/96

[56] References Cited

U.S. PATENT DOCUMENTS 3,847,756  11/1974  Statman et al. ..................... 568/699
4,943,354   7/1990  Osterberg et al. .................. 568/699

Primary Examiner—Howard T. Mars
Attorney, Agent, or Firm—Jack H. Park; Kenneth R. Priem; Carl G. Ries

[57] ABSTRACT

A method for the separation of methanol from MTBE contained in a reaction mixture comprising water, methanol, TBA and MTBE which comprises distilling the reaction mixture in the presence of added water in order to provide a distillate fraction containing most of the MTBE and a heavier distillation fraction containing most of the tertiary-butanol, water and methanol charged to the distillation column.

5 Claims, No Drawings

PURIFICATION OF METHYL TERTIARY-BUTYL ETHER

BACKGROUND OF THE INVENTION

1. Technical Field of the Invention

This invention relates to a method for the purification of methyl tertiary-butyl ether, more commonly referred to as MTBE. More particularly, this invention relates to a method for the separation of methanol from MTBE by distillation in the presence of water.

MTBE is typically produced from a refinery stream containing isobutylene in a $C_4$-$C_5$ diluent and methanol. In the separation of the unreacted methanol in the reactor effluent, the $C_4$-$C_5$ diluent acts as an azeotroping agent to selectively remove the small amount of unreacted methanol into the overhead product of the first distillation column. The bottoms product of this column is fairly pure MTBE contaminated with only small amounts of methanol, t-butanol, and other impurities.

In the one-step MTBE process, t-butanol and methanol are reacted to product MTBE and water. A portion of the t-butanol fed to the reactor system is dehydrated to form isobutylene, which also produces additional amounts of water. The relatively large concentration of water in the reactor effluent does not permit the hydrocarbon-methanol azeotrope to preferentially form as in the typical process described above. Therefore, the bottoms product of the isobutylene removal distillation column contains water, unreacted t-butanol, and essentially all of the methanol. This is a disadvantage in the next column since MTBE forms an unfavorable azeotrope with methanol, making it very difficult to produce an MTBE product relatively free of methanol.

In the present invention, an additional amount of water is added to the second distillation column to break the MTBE-methanol azeotrope and to produce an MTBE overhead product much reduced in the concentration of the methanol contaminant.

2. Prior Art

In U.S. Pat. No. 4,820,877, spearation of methanol from MTBE is accomplished by using a refinery fuel gas to enhance the separation of methanol into the overhead stream of a distillation column.

In U.S. Pat. No. 4,814,517, separation of methanol from MTBE is accomplished by using a silica gel to preferentially adsorb methanol from an MTBE stream and by periodically regenerating the silica gel.

In U.S. Pat. No. 4,798,674, separation of methanol from MTBE is accomplished by using a membrane of crosslinked polyvinyl alcohol or a quaternary ammonium ion resin. Methanol preferentially permeates through the membrane increasing the MTBE concentration of the charge liquid.

In U.S. Pat. No. 4,759,850, separation of methanol from MTBE is accomplished by reverse osmosis.

In U.S. Pat. No. 4,440,963, separation of methanol from MTBE is accomplished by adding an agent such as 2-methyl pentane or Freon 113 to form an azeotrope with methanol. This azeotrope is recovered overhead giving a methanol-free MTBE bottoms product.

SUMMARY OF THE INVENTION

In accordance with the present invention, a reaction product is prepared by the reaction of methanol with tertiary-butanol which comprises MTBE, tertiary-butanol (TBA), methanol and water, the reaction product is charged to a distillation zone such as a distillation column, and fractionated therein by simple distillation in the presence of added water to thereby form an overhead fraction containing substantially all of the MTBE and charged to the distillation column and a heavier distillation fraction, such as a bottoms fraction, containing most of the water, t-butanol and methanol charged to the distillation zone.

More particularly, this invention is directed to a process wherein a reaction product prepared by the reaction of methanol with TBA, such as the process disclosed in U.S. Pat. No. 4,144,138, and comprising water, methanol, TBA and MTBE and containing from about 2 to about 10 wt. % of water, from about 20 to about 40 wt. % of methanol, from about 20 to about 50 wt. % of TBA and from about 10 to about 30 wt. % of MTBE is fractionated by simple distillation in a distillation column in the presence of an additional 10 to 30 wt. % of water, based on the total weight of the feed to the column, to thereby provide a distillate fraction containing most of the MTBE and only a minor amount of methanol, and a heavier distillation fraction containing most of the water, methanol and TBA charged to the column.

EXAMPLES

EXAMPLE 1

In distillation run 6637-26-8, a feed containing 7.1 lbs. of water, 34.6 lbs. of methanol, 47.0 lbs. of t-butanol, and 20.4 lbs. of MTBE was fed over a 22 hour period to a 30 theoretical tray distillation column operating at an external reflux ratio of 3:1. An overhead product containing 17.8 lbs. of MTBE, a very small amount of t-butanol, 2.8 lbs. of methanol, and no detectable amount of water was obtained. A bottoms product containing 7.1 lbs. of water, 32.1 lbs. of methanol, 48.0 lbs. of t-butanol, and 3.3 lbs. of MTBE was obtained.

The overhead product contained 13.4 wt. % methanol.

EXAMPLE 2

In distillation run 6637-26-29, a feed containing 4.8 lbs. of water, 23.4 lbs. of methanol, 31.8 lbs. of t-butanol, and 13.8 lbs. of MTBE was fed over a 15 hour period to a 30 theoretical tray distillation column operating at an external reflux ratio of 3:1. An overhead product containing 16.3 lbs. of MTBE, 0.2 lbs. of t-butanol, 3.1 lbs. of methanol, and no detectable water was obtained. A bottoms product containing 5.0 lbs. of water, 22.5 lbs. of methanol, and 33.4 lbs. of t-butanol, and 2.0 lbs. of MTBE was obtained.

The overhead product contained 15.5 wt. % methanol.

In contrast, Examples 3, 4 and 5 show the advantage of using water in an extractive distillation to produce an MTBE overhead product much reduced in methanol content.

EXAMPLE 3

In distillation run 6637-37-4, a feed containing 29.1 lbs. of water, 19.3 lbs. of methanol, 12.6 lbs. of t-butanol, and 30.2 lbs. of MTBE was fed over a 20 hour period to a 30 theoretical tray distillation column operating at an external reflux ratio of 5:1. In addition, 28.5 lbs. of additional water was fed over the same time period to the column at a point above the feed point of the above feed, but below the condenser. An overhead product containing 30.1 lbs. of MTBE, 5.0 lbs. of t-butanol, 1.8 lbs. of methanol, and 1.4 lbs. of water was obtained. A bottoms product of 55.0 lbs. of water, 17.6 lbs. of methanol, and 8.8 lbs. of t-butanol containing no detectable MTBE was obtained.

The overhead product contained 4.5 wt. % methanol.

EXAMPLE 4

In distillation run 6637-16-28, a feed containing 19.7 lbs. of water, 8.2 lbs. of methanol, 7.4 lbs. of t-butanol, and 3.6 lbs. of MTBE was fed over a 8 hour period to a 30 theoretical tray distillation column operating at an external reflux ratio of 5:1. In addition, 12.0 lbs. of additional water was fed over the same time period to the column at a point above the feed point of the above feed, but below the condenser. An overhead product containing 3.3 lbs. of MTBE, 0.7 lbs. of t-butanol, no detectable methanol, and 0.3 lbs. of water was obtained. A bottoms product of 33.9 lbs. of water, 8.8 lbs. of methanol, and 7.4 lbs. of t-butanol, and 0.2 lbs. of MTBE was obtained.

The overhead product contained 0.0 wt. % methanol.

EXAMPLE 5

In distillation run 6637-13 27, a feed containing 22.5 lbs. of water, 18.5 lbs. of methanol, 17.2 lbs. of t-butanol, and 11.0 lbs. of MTBE was fed over a 14 hour period to a 30 theoretical tray distillation column operating at an external reflux ratio of 5:1. In addition, 20.3 lbs. of additional water was fed over the same time period to the column at a point above the feed point of the above feed, but below the condenser. An overhead product containing 9.8 lbs. of MTBE, 2.0 lbs. of t-butanol, 0.6 lbs. of methanol, and 1.6 lbs. of water was obtained. A bottoms product of 44.2 lbs. of water, 18.6 lbs. of methanol, and 16.7 lbs. of t-butanol, and containing no detectable MTBE was obtained.

The overhead product contained 4.4 wt. % methanol.

Example 6 shows that the standard practice of using a $C_4$–$C_5$ diluent to remove the unreacted methanol from the MTBE product does not work well in the one-step MTBE process.

EXAMPLE 6

In distillation run 6637-21-7, a feed containing 6.2 lbs. of water, 30.9 lbs. of methanol, 42.4 lbs. of t-butanol, 2.6 lbs. of isobutylene, and 19.6 lbs. of MTBE was fed over a 30 hour period to a 30 theoretical tray distillation column operating at an external reflux ratio of 4:1. An overhead product containing 2.9 lbs. of isobutylene, 0.6 lbs. of MTBE, and 0.2 lbs. of methanol was obtained. A bottoms product containing 5.7 lbs. of water, 31.0 lbs. of methanol, 0.4 lbs. of isobutylene, 41.0 lbs. of t-butanol, and 19.9 lbs. of MTBE was obtained.

As can be seen, very little of the feed methanol was removed in the overhead product.

The results of the foregoing experiments are summarized in Tables 1, 2 and 3.

TABLE 1

Feed Composition

| Exp. No. | 26-8 | | 26-9 | | 37-4 | | 16-28 | | 13-27 | | 21-7 | |
|---|---|---|---|---|---|---|---|---|---|---|---|---|
| | lbs. | wt. % | lbs. | wt. % | lbs. | wt. % | lbs. | wt. % | lbs. | wt. % | lbs. | wt. % |
| Water | 7.1 | 6.5 | 4.8 | 6.5 | 57.6 | 48.1 | 31.7 | 62.3 | 42.8 | 48.0 | 6.2 | 6.0 |
| Methanol | 34.6 | 31.7 | 23.4 | 31.7 | 19.3 | 16.4 | 8.2 | 16.1 | 18.5 | 20.7 | 30.9 | 30.4 |
| TBA[1] | 47.0 | 43.0 | 31.8 | 43.1 | 12.6 | 10.5 | 7.4 | 14.5 | 17.2 | 19.2 | 42.4 | 41.7 |
| MTBE[2] | 20.4 | 18.3 | 13.8 | 18.7 | 30.2 | 25.2 | 3.6 | 7.0 | 11.0 | 12.3 | 19.6 | 19.3 |
| IB[3] | — | — | — | — | — | — | — | — | — | — | 2.6 | 2.6 |
| Total | 109.1 | 99.5 | 73.8 | 100.0 | 119.7 | 100.2 | 50.9 | 99.9 | 89.5 | 100.2 | 101.7 | 100.0 |

[1] Tertiary butyl alcohol
[2] Methyl tertiary-butyl ether
[3] Isobutylene

TABLE 2

Overhead Composition

| Exp. No. | 26-8 | | 26-9 | | 37-4 | | 16-28 | | 13-27 | | 21-7 | |
|---|---|---|---|---|---|---|---|---|---|---|---|---|
| | lbs. | wt. % | lbs. | wt. % | lbs. | wt. % | lbs. | wt. % | lbs. | wt. % | lbs. | wt. % |
| Water | — | — | — | — | 1.4 | 3.7 | 0.3 | 7.0 | 1.6 | 11.4 | — | — |
| Methanol | 2.8 | 13.6 | 3.1 | 15.8 | 1.8 | 4.6 | — | — | 0.6 | 4.3 | 0.2 | 5.4 |
| TBA[1] | — | — | 0.2 | 1.0 | 5.0 | 13.1 | 0.7 | 16.3 | 2.0 | 14.3 | — | — |
| MTBE[2] | 17.8 | 86.4 | 16.3 | 83.2 | 30.1 | 78.6 | 3.3 | 76.7 | 9.8 | 70.0 | 0.6 | 16.2 |
| IB[3] | — | — | — | — | — | — | — | — | — | — | 2.9 | 78.4 |
| Total | 20.6 | 100.0 | 19.6 | 100.0 | 38.3 | 100.0 | 4.3 | 100.0 | 14.0 | 100.0 | 3.7 | 100.0 |

[1] Tertiary butyl alcohol
[2] Methyl tertiary-butyl ether
[3] Isobutylene

TABLE 3

Bottoms Composition

| Exp. No. | 26-8 | | 26-9 | | 37-4 | | 16-28 | | 13-27 | | 21-7 | |
|---|---|---|---|---|---|---|---|---|---|---|---|---|
| | lbs. | wt. % | lbs. | wt. % | lbs. | wt. % | lbs. | wt. % | lbs. | wt. % | lbs. | wt. % |
| Water | 7.1 | 7.8 | 5.0 | 7.9 | 55.0 | 67.6 | 33.9 | 64.8 | 44.2 | 55.5 | 5.7 | 5.8 |
| Methanol | 32.1 | 35.7 | 22.5 | 35.8 | 17.6 | 21.6 | 8.8 | 16.8 | 18.6 | 23.3 | 31.0 | 31.6 |
| TBA[1] | 48.0 | 53.0 | 33.4 | 53.1 | 8.8 | 10.8 | 7.4 | 14.1 | 16.7 | 21.0 | 41.0 | 41.8 |
| MTBE[2] | 3.3 | 3.6 | 2.0 | 3.2 | — | — | 0.2 | 0.3 | — | — | 19.9 | 20.2 |
| IB[3] | — | — | — | — | — | — | — | — | — | — | 0.4 | 0.4 |

TABLE 3-continued

| | Bottoms Composition | | | | | | | | | | | |
|---|---|---|---|---|---|---|---|---|---|---|---|---|
| | Exp. No. | | | | | | | | | | | |
| | 26-8 | | 26-9 | | 37-4 | | 16-28 | | 13-27 | | 21-7 | |
| | lbs. | wt. % | lbs. | wt. % | lbs. | wt. % | lbs. | wt. % | lbs. | wt. % | lbs. | wt. % |
| Total | 90.5 | 100.1 | 62.9 | 100.0 | 81.4 | 100.0 | 52.3 | 98.0 | 79.7 | 99.8 | 98.2 | 99.8 |

[1] Tertiary butyl alcohol
[2] Methyl tertiary-butyl ether
[3] Isobutylene

The distillation column to be used in accordance with the present invention is suitably a simple distillation column containing at least about 5 theoretical trays and preferably from about 10 to about 60 theoretical trays. The column is suitably operated at a pressure of from about 10 psia to about 100 psia. The temperature conditions will suitably include a reboiler temperature of about 55° C. to about 150° C. and a condenser temperature of about 45° C. to about 135° C.

The additional water added to the distillation column in accordance with the process of the present invention is preferably added separately from the feedstock at a point in the column above the feed but below the condenser, such as a point at least about 2 theoretical trays above the point at which the feedstock is introduced.

Having thus described out invention, what is claimed is:

1. In a process for the production of methyl tertiary-butyl ether (MTBE) wherein methanol is reacted with tertiary-butanol (TBA) in a reaction zone to form a reaction product comprising water, methanol, TBA and MTBE, and wherein the reaction mixture is charged to a simple distillation column to separate the MTBE from the methanol, the improvement which comprises adding to the reaction mixture from about 10 to about 30 wt. % of water, based on the total weight of the feed to the distillation column to thereby provide a distillate fraction containing substantially all of the MTBE charged to the distillation column and a heavier distillation fraction comprising most of the water and tertiary-butanol charged to the distillation column.

2. A method as in claim 1, wherein the distillation column contains from about 10 to about 60 theoretical trays, wherein the feedstock is added about 10 theoretical trays above the bottom of the tower and wherein the added water is added at least about 2 theoretical trays above the point of introduction of the feed.

3. A method as in claim 2 wherein the distillation column is operated at a pressure of about 10 psia to about 100 psia.

4. A method as in claim 3 wherein the distillation column contains a reboiler and a condenser and wherein the reboiler is maintained at a temperature of about 55° C. to about 150° C. and the condenser is maintained at a temperature of about 45° C. to about 135° C.

5. In a method wherein methanol is reacted with tertiary-butanol to provide a reaction mixture comprising from about 2 to 10 wt. % of water, from about 20 to about 40 wt. % of methanol, from about 20 to about 50 wt. % of tertiary butyl alcohol and from about 10 to about 30 wt. % of methyl tertiary-butyl ether (MTBE), the improvement for separating the methanol from the MTBE which comprises:

charging said reaction mixture to a simple distillation column containing from about 10 to about 60 theoretical trays at a point in the distillation column from about 10 to about 30 theoretical trays from the bottom of the tower, said tower containing a reboiler and a condenser, adding from about 10 to about 30 wt. % of water, based on the weight of the feedstock to the distillation column at a point from about 2 to about 10 theoretical trays above the point of introduction of the feedstock, operating the distillation column at a pressure of from about 10 psia to about 100 psia, at a reboiler temperature of about 55° C. to about 150° C. and a condenser temperature of about 45° C. to about 135° C., and withdrawing from the column an overhead fraction comprising most of the MTBE charged to the distillation column and a bottoms fraction comprising most of the methanol, water and tertiary-butanol charged to the distillation column.

* * * * *